United States Patent
Boudenne et al.

(10) Patent No.: US 8,778,693 B2
(45) Date of Patent: Jul. 15, 2014

(54) KIT FOR DETECTING FUNCTIONAL CARBOXYL GROUPINGS

(75) Inventors: Jean-Luc Boudenne, Marseilles (FR); Bruno Coulomb, Bouc Bel Air (FR); Fabien Robert-Peillard, Communay (FR); Edwin Barco Palacio, Marseilles (FR)

(73) Assignees: Universite d'Aix Marseille, Marseille Cedex (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/575,472

(22) PCT Filed: Jan. 26, 2011

(86) PCT No.: PCT/FR2011/000048
§ 371 (c)(1),
(2), (4) Date: Jul. 26, 2012

(87) PCT Pub. No.: WO2011/092400
PCT Pub. Date: Aug. 4, 2011

(65) Prior Publication Data
US 2012/0309097 A1 Dec. 6, 2012

(30) Foreign Application Priority Data
Jan. 28, 2010 (FR) ..................... 10 00340

(51) Int. Cl.
*G01N 21/64* (2006.01)
*G01N 21/00* (2006.01)
(52) U.S. Cl.
USPC ........................... 436/129; 436/128; 436/127
(58) Field of Classification Search
USPC ........................ 436/129, 128, 127
See application file for complete search history.

(56) References Cited

U.S. PATENT DOCUMENTS 3,980,433 A 9/1976 Tamura

FOREIGN PATENT DOCUMENTS

| WO | 03/036260 A2 | 5/2003 |
| WO | 2010/010242 A2 | 1/2010 |

OTHER PUBLICATIONS

Kibler M, et al: "New derivatization method for carboxylic acids in aqueous solution for analysis by capillary electrophoresis and laser-induced fluorescence detection", Journal of Chromatography, Elsevier Science Publishers B. V. NL LNKD-DOI: 10.1016/S0021-9673 (99) 00012-6, vol. 836, No. 2, Mar. 26, 1999, pp. 325-331 XP004161582 ISSN:0021-9673.

Sano A et al.: "Fluorescence quenching properties and chemiluminescence responses of alpha-ketothiols derivatized with o-phthalaldehyde and primary amino compounds", Luminescence, John Wiley & Sons LTD, GB LNKD-DOI: 10.1002/BIO.592, vol. 16, No. 1, Jan. 1, 2001, pp. 25-28, XP002518444, ISSN: 1522-7235.

Montigny Pierre De, et al. "Naphthalene-2,3-Dicarboxaldehyde/ Cyanide Ion: A Rationally Designed Fluorogenic Reagent for Primary Amines", Analytical Chemistry, Amercian Chemical Society, US LNKD-DOI: 10.1021/A000135A007,vol. 59, No. 8, Apr. 15, 1987, pp. 1096-1101, XP002518446, ISSN: 0003-2700.

Kobayashi M, et al.: "Water-Soluble Carbodiimide for the Fluorescent Measurement of the Carboxyl Group Produced by Enzyme Reactions", Analytical Biochemistry, Academic Press INC, New York LNKD-DOI: 10.1006/ABIO.1994.1256, vol. 219, No. 2, Jun. 1, 1994 pp. 189-194, XP024763270, ISSN: 0003-2697.

*Primary Examiner* — Christine T Mui
(74) *Attorney, Agent, or Firm* — Lucas & Mercanti, LLP

(57) ABSTRACT

A subject of the invention is a kit for the identification, characterization and quantification by a single detection of the carboxylic, thiol and amine functional groups contained in a sample.

25 Claims, 1 Drawing Sheet

KIT FOR DETECTING FUNCTIONAL CARBOXYL GROUPINGS

CROSS-REFERENCE TO RELATED APPLICATIONS

This application is a 371 of PCT/EP2011/000048 filed Jan. 26, 2011, which in turn claims the priority of FR 1000340 filed Jan. 28, 2010, the priority of both applications is hereby claimed and both applications are incorporated by reference herein.

The invention relates to the field of environmental quality monitoring, in particular to soil quality analysis, and even more particularly to the management of waste and wastewater, in particular within sludge treatment units using anaerobic processes (methanization for example), in the context of the operation of biological treatment plants as well as with respect to effluents and wastewaters from the agri-food industry, or also landfill sites, but also to the field of health.

The invention relates to a kit for the identification, characterization and quantification by a single detection of the carboxylic, thiol and amine functional groups contained in a sample, as well as the use of said kit for identifying, characterizing and quantifying, by a single detection, the carboxylic, thiol and amine functional groups contained in a sample.

The identification of the nature of dissolved organic compounds (generally grouped under the inclusive term dissolved organic carbon, DOC) is limited to a semi-speciation making it possible to determine the content of hydrophilic and hydrophobic compounds (separation over macroporous resins by gel filtration then by ultrafiltration) to estimate a humification index or, in the best cases, of different fractions produced by sequential extractions on ionic or non-ionic resins making it possible to define contents of more or less bioavailable compounds depending on the extractants used.

Downstream of these extraction steps, a characterization of the functional groups is sometimes carried out by near-infrared spectroscopy (NIRS), carbon nuclear magnetic resonance ($^{13}$C-NMR), or by pyrolysis coupled with gas chromatography and detection by mass spectrometry (Pyr-GC-MS).

The carboxylic function can be estimated by separate quantification of the short-chain carbon-containing aliphatic acids (formic, lactic, pyruvic, propionic, succinic, glyceric and citric acids) by ion chromatography or liquid chromatography generally coupled with an electrolytic conductivity or UV-visible spectrophotometric detector. Liquid chromatography (HPLC) can also be coupled with mass spectrometry detectors (LC/MS). Gas chromatography (GC) has also been used, coupled with flame ionization detectors or mass spectrometers, the carboxylic acids being quantified after a step of derivatization and a step of liquid-liquid or solid-liquid extraction. There can also be mentioned more complex couplings such as GC/EI-MS (electron impact mass spectrometry) or CG/CI-MS (mass spectrometry with chemical ionization) with quantification after solid-phase microextraction.

More recently, carboxylic acids have been analyzed by capillary electrophoresis (CE), Some of these methods can show significant interference with di- or trivalent metallic cations, which can be reduced by adding EDTA before analysis, Souza et al. (S. R. Souza et al. *Journal of Chromatography A* 796, 335-346, 1998) compared the analysis of 7 main carboxylic acids by ion chromatography (IC) and capillary electrophoresis coupled with a UV detector and concluded that the choice of analytical method depended on the type of sample analyzed, as the IC method has the drawback of poor separation of the different acids, the CE method lacking sensitivity.

In order to improve the analytical characteristics of these chromatographic methods, many studies have been oriented towards the derivatization of carboxylic acids, in order to form a by-product having for example a very intense fluorescence and allowing very sensitive quantification. In order to achieve sufficient derivatization yields, it is first necessary to carry out the activation of the carboxylic group, using reagents such as carbodiimides, pyridinium salts or disulphites. For the derivatization, many fluorescent compounds can be used. The most usual are bromoalkyls, diazomethanes, hydrazines and amines.

The thiol function is contained in many sulphur-containing compounds of biological or ecological significance, such as glutathione, phytochelatins, cysteine. These compounds are very often produced by plants or phytoplankton following stress induced by the presence of metallic and/or organic micropollutants. Kawakami at at (S. K. Kawakami et al. *Trends in Analytical Chemistry*, 25, 2, 133-142, 2006) carried out a review of the main methods of detection of thiols in different biological or environmental matrices. Thiols can be assayed directly by different electrochemical methods: polarography, voltametry amperometry. These methods however have the drawbacks of selectivity and matrix interference. More conventionally, thiols are generally assayed indirectly after derivatization and separation by liquid chromatography or capillary electrophoresis with detection by UV-visible spectrometry or mass spectrometry. Lock and Davis (J. Lock, J. Davis *Trends in Analytical Chemistry*, 21, 12, 807-815, 2002) published a review of the different derivatization agents mainly used for the assay of thiols: haloacetamide, maleimides, benzoxadiazoles, isoindoles.

Assay of the amine function is generally carried out by separation of the amine compounds by liquid chromatography or capillary electrophoresis after derivatization. A. Önal (A. Önal *Food Chemistry* 103, 1475-1486, 2007) recently published a bibliographical review detailing the various methods of amine assay of biological interest. This shows that derivatization of amines is mainly carried out by 4 compounds: o-phthalaldehyde (OPA), 5-dimethylaminonaphthalene-1-sulphonyl chloride (DNS), 4-chloro-7-nitrobenzofuran or 1,2-naphthoquinone-4-sulphonate (NOS). The detection is carried out by a UV-visible or fluorimetric detector. There are only a few methods in which the prior derivatization step is not used, the separation being carried out by liquid chromatography or capillary electrophoresis, and detection by conductometric analysis, enzymology or amperometry. The method most used remains however the separation of the OPA derivatives. OPA reacts with primary amines in the presence of a thiol compound, in a borate-buffered medium. Recent research has been carried out to determine which thiol compound gives stable derivatives, or also to synthesize reagents reacting with the amines and forming more absorbent or more fluorescent derivatives. However, a number of these newly synthesized compounds are not commercial.

It is therefore noted that most of the methods of quantification of the carboxylic compounds, thiols or amines pass through a step of chromatographic or electrophoretic separation. This leads to relatively long analysis times (10 to 30 minutes depending on the method). Furthermore, these methods utilize equipment that is quite complex to use and can only be utilized in the laboratory.

There is therefore a need for methods of identification, characterization and quantification by a single detection of the carboxylic, thiol and amine functional groups contained in a single sample that are quick, economical and above all can be used on site without the need for heavy and costly equipment.

This is one of the purposes of the invention.

Thus a subject of the invention is a kit for the identification, characterization and quantification by a single detection of the carboxylic, thiol and amine functional groups contained in a sample, comprising
- a. at least one primary activating agent of the carbons bearing the carboxylic functional groups;
- b. at least one fluorescent primary amine;
- c. at least one compound of the dialdehyde family;
- d. at least one non-fluorescent amine;
- e. at least one pH-modulator buffer;
- f. at least one non-fluorescent thiol.

The kit according to the invention requires only reasonable investment in the simple apparatus making it easy to utilize on-site.

The utilization of said kit, although not allowing a separate quantification of all the carboxylic, amine or thiol compounds contained in the sample, allows the global quantification of the functional groups in question (total concentration of thiols and total concentration of amines, total concentration of aliphatic carboxylic acids: Volatile Fatty Acids=VFA) and within a few minutes gives a reliable indication of the quality of water, soil or waste, or also the operational status of a treatment process.

According to the invention, whatever the method used, it is possible to carry out fluorescence measurements by using at least one excitation/measurement wavelength pair but several pairs can also be used, advantageously two pairs.

According to the invention, the primary activating agent of We carbons bearing the carboxylic functional groups can be chosen from the carbodiimides, such as for example 1-ethyl-3-(3-dimethylaminopropyl)-carbodiimide (EDC) or N-cyclohexyl-N'-(2-morpholinoethyl)carbodiimide methyl-p-toluenesulphonate (CMC), or also N,N'-dicyclohexylcarbodiimide (DCC), N,N'-diisopropylcarbodiimide (DIC), bis(trimethylsilyl) carbodiimide (BTSC), and preferably EDC or CMC, very preferably EDC.

According to a variant of the invention, the kit can also comprise at least one secondary activating agent, activating the carbodiimides, themselves activating the carbons bearing the carboxylic functional groups, which can be chosen from N-hydroxysuccinimide (NHS) or 1-hydroxybenzotriazole (HOBT) or tetrafluorophenol (TTP) or 1-hydroxy-7-azabenzotriazole (HOAT), preferably HOAT.

According to the invention, the fluorescent primary amine can be a compound of the benzofurazan family, or the aminophenanthrene family, or the coumarin family, or the family of the "dansyl" derivatives, N-1-ethylenediaminonaphthalene (EDAN), or 5-aminofluorescein (5-AF), or monodansylcadaverine (MDC) or Nile blue chloride (NBCl), preferably EDAN.

According to another variant of the invention, the kit can also comprise an extraction solvent of the fluorescent primary amine, which can be a water-immiscible organic solvent, such as for example methyl-tert-butyl ether (MTBE), dibutyl ether (DBE), ethyl acetate, cyclohexane or also dichloromethane, preferably MTBE.

According to the invention, the compound of the dialdehyde family can for example be o-phthaldialdehyde (OPA) or naphthalene-2,3-dicarboxyaldehyde (NDA), preferably OPA.

Still according to the invention, the non-fluorescent amine can be 2-aminoethanol, glycine, valine, leucine, butylamine, tert-butylamine or also N-ϵ-acetyl-L-lysine, preferably 2-aminoethanol.

Further according to the invention, the pH modulator can be a borate buffer, a phosphate buffer, a citrate buffer, an organic buffer such as HEPES (1-piperazineethane sulphonic acid) or also a TRIS (tris(hydroxymethyl)aminoethane) buffer, preferably a borate buffer for the determination of the thiols and the amines and a phosphate buffer for the determination of the carboxylic acids.

Still according to the invention, the non-fluorescent thiol can be chosen from many thiol compounds such as glutathione, mercaptoacetic (or thioglycolic) acid, cysteine, mercaptoethanesulphonic acid, 2-mercaptoethanol, 3-mercaptopropionic acid, 2-mercaptopropionic acid, mercaptosuccinic acid, N-acetyl-cysteine (NAG), methanethiol, monothioglycerol, sulphite salts or also thiosulphate salts, preferably mercaptoethanol.

According to another variant of the invention, the kit can moreover comprise at least one reducing agent that can advantageously be chosen from the compounds of the family of hydrazines, hydrides, thiols such as for example dithioerythritol (DTE) or dithiothreitol (DTT), or trialkylphosphines including tri-n-butylphosphine (TBP) or also tris-2-carboxyethyl-phosphine hydrochloride (TCEP), preferably tris-2-carboxyethyl-phosphine hydrochloride.

According to another variant of the invention, the kit can moreover comprise a dissolution buffer for the sample to be tested, said buffer having a pH that can be comprised between 3.5 and 5.5, preferably between 4.0 and 5.0, very preferably 4.5.

According to another variant of the invention, the kit can moreover comprise an acid such as for example hydrochloric acid (HCl).

According to yet another variant of the invention, the kit can moreover comprise an inorganic base, such as soda (NaOH).

According to yet another variant of the invention, the kit can moreover comprise a fluorescence activator such as a surface-active agent (or surfactant) or a compound of the cyclodextrin family, preferably a surface-active agent, at a concentration comprised between 100 and 120% of its CMC (Critical Micelle Concentration), very preferably 100% of the CMC.

According to another variant of the invention, the kit can also comprise a halogenated active agent, which can be sodium hypochlorite, N-chlorosuccinimide or also a compound of the chloramine family.

The kit according to the invention can be presented in all the desired forms compatible with marketing. Advantageously it can be presented in the form of a multi-well plate, each well comprising a sufficient quantity of each of the elements necessary for the identification, characterization and quantification by a single detection of the carboxylic, thiol and amine functional groups contained in a sample as described previously. According to this variant, each well can contain the elements necessary for the identification, characterization and quantification by a single detection of the carboxylic, thiol and amine functional groups contained in a sample in sufficient quantity for one analysis. Still according to this variant the elements necessary for the identification, characterization and quantification by a single detection of the carboxylic, thiol and amine functional croups contained in a sample can be in liquid form, in which case the support plate can be provided with a means for closing the wells, or also in freeze-dried form.

The kit according to the invention can also be incorporated into an in-line analyzer.

A subject of the invention is also the use of a kit as described previously, for the identification, characterization and quantification by a single detection of the carboxylic, thiol and amine functional groups contained in a sample.

According to the invention, the kit for the identification, characterization and quantification by a single detection of carboxylic functional groups is simple, the solubility of the different constituents and the reactivity of the reagents in the kit are improved. Moreover, the volume of sample necessary for the reaction is reduced and interferences are limited.

This kit can be utilized in a method for the identification, characterization and quantification by a single detection of carboxylic functional groups (elsewhere in the text called method for the determination of the carboxylic groups) in which a. In a first step a sample previously taken for analysis is mixed with a solution for dissolving said sample to be tested, previously prepared by mixing at least one buffer, a primary activating agent of the carbons bearing the carboxylic functional groups and a secondary activating agent, and this mixture is incubated for a time comprised between 2 and 8 minutes, preferably between 4 and 6 minutes;

b. in a second step, a fluorescent primary amine dissolved in ultrapure water or in a buffer is added to the mixture obtained in the first step;

c. in a third step, there is added to the mixture obtained in the second step, a compound chosen from the members of the dialdehyde family, such as naphthalene-2,3-dicarboxyaldehyde (NDA) or o-phthaldialdehyde (OPA), preferably OPA, previously dissolved in a basic-pH aqueous buffer (solution of borate, phosphate, sodium hydroxide, etc.) at a pH comprised between 6 and 11, preferably between 8 and 9.5, very preferably between 8.5 and 9.5 or in a mixed (organic solvent/water) solvent, at a pH comprised between 5 and 9, preferably 6.5, or in an organic solvent, preferably in an organic solvent.

d. in a fourth step, the induced fluorescence of the previously-obtained mixture is measured at a wavelength comprised between 390 and 490 nm, preferably 442 nm, after excitation at a wavelength comprised between 300 and 350 nm, preferably 335 nm:

e. in a fifth step, the value obtained in the fourth step is referred to a calibration curve previously established under the same conditions.

According to the invention, in the first step of the method for determination of the carboxylic groups, the buffer of the solution for dissolving the sample to be tested can be a phosphate buffer at a concentration that can be comprised between 2 mM and 60 mM, preferably between 5 mM and 20 mM, very preferably 10 mM.

Still in the first step of said method, the solution for dissolving the sample to be tested can have a pH comprised between 2 and 6, preferably between 3.0 and 4.0, very preferably 3.5.

Still in the first step of the method for determination of the carboxylic groups, the primary activating agent of the carbons bearing the carboxylic functional groups can be chosen from the compounds of the carbodiimide family, advantageously from 1-ethyl-3-(3-dimethylaminopropyl)-carbodiimide (EDC) or N-cyclohexyl-N'-(2-morpholinoethyl)carbodiimide methyl-p-toluenesulphonate (CMC), or also N,N'-dicyclohexylcarbodiimide (DCC), N,N'-diisopropylcarbodiimide (DIC), bis(trimethylsilyl)carbodiimide (BTSC). Preferably the primary activating agent of the carbons bearing the carboxylic functional groups can be EDC or CMC, very preferably EDC. Said primary activating agent can be at a concentration of between 0 and 100 mg per ml of sample to be analyzed, preferably from 25 to 50 mg and very preferably 37.5 mg per ml of sample to be analyzed, dissolved in a water-miscible organic solvent. In the case of EDC, the latter can preferably be dissolved in ethanol.

According to the invention, still in said first step, the secondary activating agent of the primary activating agent described previously can be chosen from NHS (N-hydroxysuccinimide) or 1-hydroxybenzotriazole (HOBT) or tetrafluorophenol (TTP) or 1-hydroxy-7-azabenzotriazole (HOAT), preferably HOAT. Said secondary activating agent can be at a concentration comprised between 0 and 50 mg per ml of sample to be analyzed, preferably between 15 and 30 mg and very preferably 25 mg per ml of sample to be analyzed, dissolved in the solution for dissolving the sample described in the first step.

According to the invention, in the second step of the method for determination of the carboxylic groups, the fluorescent primary amine can be a compound of the benzofurazan family, or the aminophenanthrene family, or the coumarin family, or the family of the "dansyl" derivatives, N-1-ethylenediaminonaphthalene (EDAN), or 5-aminofluorescein (5-AF), or monodansylcadaverine (MDC) or Nile blue chloride (NBCl), preferably EDAN. Said fluorescent primary amine can be at a concentration comprised between 0 and 100 mg per ml of sample to be analyzed, preferably between 25 and 50 mg per ml of sample to be analyzed, very preferably 37.5 mg per ml of sample to be analyzed, advantageously mixed with the liquid sample, at a pH comprised between 5.5 and 11.0, preferably between 8.0 and 9,0, very preferably 8.7.

According to the invention, still in the second step of the method for determination of the carboxylic groups, the dissolution buffer of the fluorescent primary amine can be a borate buffer.

According to the invention, in the third step of the method for determination of the carboxylic groups, the NDA or the OPA is preferably dissolved in an organic solvent, very preferably in ethanol.

Still in this third step, the organic solvent constituting the mixed (organic solvent/water) solvent is advantageously chosen from any water-miscible organic solvent, preferably ethanol. The proportions of the organic solvent and the water are not particularly significant, however advantageously according to the invention the mixed (organic solvent/water) solvent, is preferably in the proportion 75/25, very preferably in the proportion 50/50.

According to the invention, in the third step of the method for determination of the carboxylic groups, the dialdehyde can be at a concentration comprised between 0 and 200 mg per ml of sample to be analyzed, preferably between 20 and 100 mg per ml of sample to be analyzed, very preferably 50 mg per ml of sample to be analyzed.

According to the invention, still in the third step, the pH of the mixed solvent can be adjusted with an organic or inorganic base, such as a borate, phosphate or also sodium hydroxide solution.

According to the invention, in the fourth step, it is possible to carry out fluorescence measurements by using at least one excitation/measurement wavelength pair but several pairs can also be used, advantageously two pairs.

According to the invention, in the fifth step of the method for determination of the carboxylic groups, the reference carboxylic acid for establishing said previously-established calibration curve can be chosen from any monocarboxylic acid, such as for example acetic acid, propionic acid, butyric acid, valeric acid, formic acid, lactic acid, p-hydroxybenzoic acid, preferably acetic acid.

According to the invention, the kit for the identification, characterization and quantification by a single detection of thiol functional groups (elsewhere thiol detection method) can be utilized in a method in which
   a. in a first step a sample previously taken is mixed with a compound chosen from the members of the dialdehyde family, such as naphthalene-2,3-dicarboxyaldehyde (NDA) o-phthaldialdehyde (OPA) and a non-fluorescent amine, preferably 2-aminoethanol, previously dissolved in a mixed (organic solvent/water) solvent, at a pH comprised between 6 and 11, preferably between 8 and 9.5, very preferably between 8.5 and 9.5;
   b. in a second step the fluorescence of the mixture obtained in the first step is measured after excitation at a wavelength of 335 nm, and measured at a wavelength of 450 nm for the identification, characterization and quantification of the monothiol functional groups;
   c. In a third step the values obtained in the second step are referred to the calibration curves previously established under the same conditions with a reference compound bearing thiol groups.

According to the invention, in the first step of the thiol detection method, the compound chosen from the members of the dialdehyde family can be naphthalene-2,3-dicarboxyaldehyde (NDA) or o-phthaldialdehyde (OPA), preferably OPA.

Similarly in this first step, the non-fluorescent amine can be 2-aminoethanol, glycine, valine, leucine, butylamine, tert-butylamine or also N-ε-acetyl-L-lysine, preferably 2-aminoethanol.

Still in this first step, the organic solvent constituting the mixed (organic solvent/water) solvent is advantageously chosen from any water-miscible organic solvent, preferably methanol. The proportions of the organic solvent and the water are not particularly significant, however advantageously according to the invention the mixed (organic solvent/water) solvent is preferably in the proportion 75/25, very preferably in the proportion 40/60.

According to a variant of the invention, in the first step of the thiol detection method a reducing agent can be added, chosen from the compounds of the family of hydrazines, hydrides, thiols such as for example dithioerythritol (DTE) or dithiothreitol (DTT), or trialkylphosphines including tri-n-butylphosphine (TBP) or also tris-2-carboxyethyl-phosphine hydrochloride (TCEP), preferably tri-n-butylphosphine, advantageously dissolved in any water-miscible organic solvent, preferably methanol or tris-2-carboxyethyl-phosphine, advantageously dissolved in an aqueous buffer, and a water-immiscible organic solvent, preferably dichloromethane, in order to reduce the oxidized thiol compounds to monothiol compounds. According to a variant of the invention, in this first step of the method, ethylene-diamine-tetraacetic acid (EDTA) can also be added in order to prevent the re-oxidation of the reduced thiols and to limit interference from metallic elements.

In the second step of the thiol detection method, the fluorescence of the aqueous phase obtained in the first step is measured after excitation at a wavelength of 335 nm, and measured at a wavelength of 450 nm for the identification, characterization and quantification of the total thiol functional groups.

According to the invention, in the second step, it is possible to carry out the fluorescence measurements by using at least one excitation/measurement wavelength pair but several pairs can also be used, advantageously two pairs.

According to a variant of the invention, in the second step of the thiol detection method, a fluorescence activator can be added, such as a surface-active agent (or surfactant) or a compound of the cyclodextrin family, preferably a surface-active agent, very preferably a BRIJ surfactant, at a concentration comprised between 100 and 120% of its CMC (Critical Micelle Concentration), very preferably 100% of its CMC.

According to the invention, in the third step of the thiol detection method, the reference compound bearing thiol groups can be chosen from mercaptoacetic (or thioglycolic) acid, cysteine, mercaptoethanesulphonic acid, 2-mercaptoethanol, 3-mercaptopropionic acid, glutathione, 2-mercaptopropionic acid, mercaptosuccinic acid, methanethiol, monothioglycerol, preferably glutathione or cysteine, very preferably cysteine.

According to the invention, the kit for the identification, characterization and quantification by a single detection of amine functional groups (elsewhere amine detection method) can be utilized in a method in which:
   a. in a first step, a sample previously taken is mixed with a compound chosen from the members of the dialdehyde family and a non-fluorescent thiol compound such as mercaptoethanol, N-acetyl-cysteine (NAC), or also 3-mercapto propionic acid, said thiol compound being previously dissolved in solution at a pH comprised between 6 and 11, preferably between 9 and 10.5, in an aqueous solvent or in a mixed organic solvent/water solvent;
   b. in a second step, the fluorescence of the mixture obtained in the first step is measured at a wavelength comprised between 430 and 460 nm after excitation at a wavelength comprised between 330 and 340 nm, for the identification, characterization and quantification of the amine functional groups;
   c. in a third step, the values obtained in the second step are referred to the calibration curves previously established under the same conditions with a reference compound bearing amine groups.

According to the invention, in the first step of the amine detection method, the compound chosen from the members of the dialdehyde family can be naphthalene-2,3-dicarboxaldehyde (NDA) or o-phthaldialdehyde (OPA), preferably OPA.

Still in this first step the non-fluorescent thiol compound can be chosen from numerous thiol compounds such as mercaptoethanol, N-acetyl-cysteine (NAC), or also 3-mercaptopropionic acid, preferably 2-mercaptoethanol.

Still in this first step, the mixed organic solvent/water solvent is advantageously constituted by a completely water-miscible organic solvent, preferably methanol.

According to the invention, in the third step of the amine detection method, the reference amine-bearing compound can be chosen from primary amines, secondary amines, tertiary amines or amino acids, preferably aminoethanol, glycine or butylamine, very preferably glycine.

According to a variant of the invention, in the first step of the amine detection method, a halogenated active agent can be added, which can be sodium hypochlorite, N-chlorosuccinimide or also a compound of the chloramine family, preferably sodium hypochlorite, in order to convert the secondary and tertiary amines to primary amines.

According to the invention, at the end of the analysis procedure the fluorescence measurement can be carried out on any fluorescence spectrophotometer, particularly on a microplate reader such as those from PERKIN ELMER or TECAN.

According to the invention, it is possible to carry out the fluorescence measurements by using at least one excitation/measurement wavelength pair but several pairs can also be used, advantageously two pairs.

According to the invention, the sample can be a sample of waste or wastewater, or soils, or sludges originating from a unit for the treatment of sludges by methanization, advantageously in anaerobic processes, a sample originating from the operation of biological treatment plants, or also a sample originating from the health field (biological fluids such as urine, blood, saliva samples, sweat, etc).

It is understood of course that one of the benefits of the kit according to the invention is that it makes it possible to carry out the identification, characterization and quantification at the same time via a single detection (fluorescence on microplate) of the carboxylic, thiol and amine functional groups contained in a sample.

Other characteristics and advantages of the invention will become more apparent from the following examples, given by way of a non-limitative illustration.

EXAMPLE 1

150 µL of a 2 mg/mL HOAT solution dissolved in 10 mM phosphate buffer is introduced into a well of a 96-well black polypropylene microplate. The pH of this solution is adjusted to a pH of 3.5. Then 8 µL of a sample of centrifuged treatment plant sludge filtered using a 0.8 µm glass fibre filter is added. The pH of this sample is adjusted to a pH comprised between 3.5 and 5.5. 18 µL of a solution of EDC at 3 mg/180 µL of ethanol is added to this solution.

After stirring and incubation at 40° C. for 4 minutes, 50 µL of a solution of EDAN at 3 mg/500 µL of 50 mM borate buffer, pH 8.7 is added. The mixture is stirred and incubated at 40° C. for 2 minutes.

Then 18 µL of a solution of OPA at 4 mg/180 µL of ethanol is added to the mixture previously obtained. The mixture is stirred and incubated at 40° C. for 12 minutes, and the fluorescence is measured using a microplate fluorescence reader at an excitation wavelength of 335 nm and an emission wavelength of 442 nm.

Figure 1:
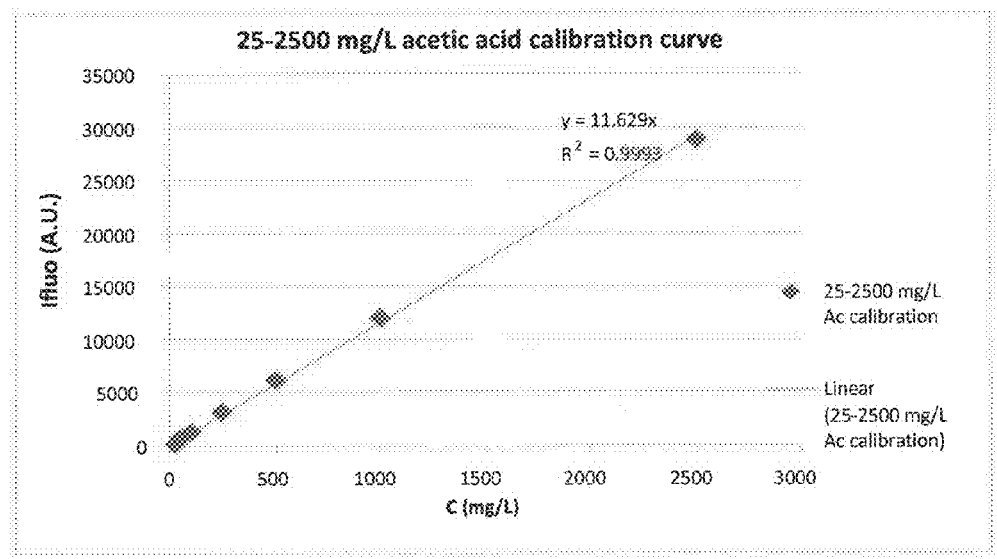
FIG. 1 shows a calibration curve established with acetic acid at concentrations comprised between 25 and 2500 mg/L. The figure shows the fluorescence intensity measured at 396 nm after excitation at 335 nm as a function of the acetic acid concentration.
Figure 2:
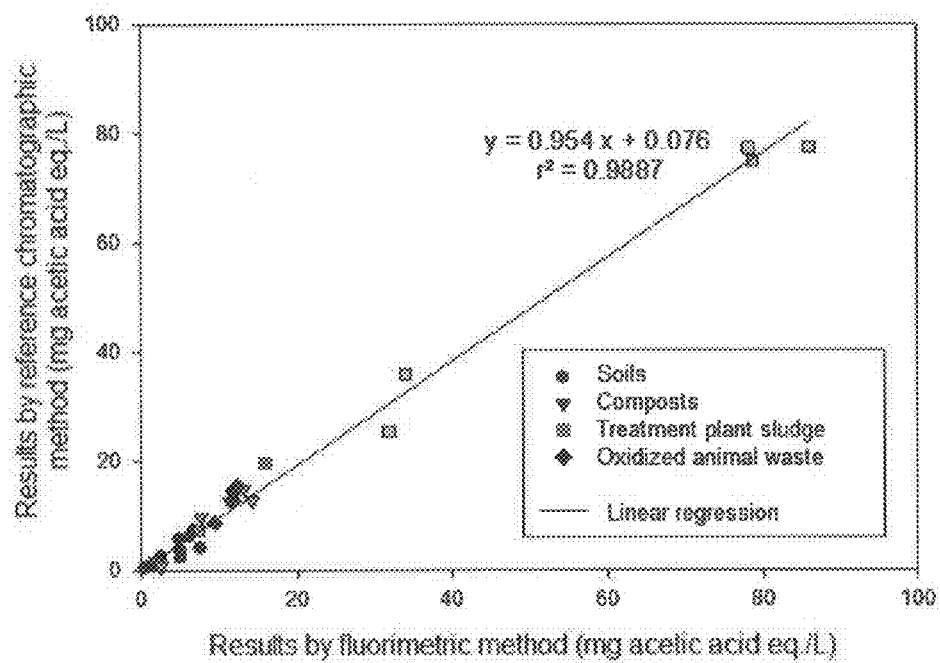
FIG. 2 shows the perfect correlation between the measurements carried out using the kit according to the invention and the measurements carried out according to the standard method (determination of these carboxylic acids by ion chromatography with detection by conductometric analysis).

In parallel, a reference curve is plotted under the same conditions as those to which the sample has been subjected with acetic acid at concentrations comprised between 25 and 2500 mg/L. This calibration curve is shown in FIG. 1. The value of the fluorescence intensity of the sample is then referred to the calibration curve (FIG. 1); it is then possible to express the result of this analysis in acetic acid equivalents and therefore to determine the number of acetic acid equivalents in the sample.

The invention claimed is:

1. Method for the identification, characterization and quantification by a single detection of carboxylic functional groups, comprising:
   a. in a first step, a sample previously taken for analysis is mixed with a solution for dissolving said sample to be tested, previously prepared by mixing at least one buffer, a primary activating agent of the carbons bearing the carboxylic functional groups and a secondary activating agent, and this mixture is incubated for a given time;
   b. in a second step, a fluorescent primary amine dissolved in ultrapure water or in a buffer is added to the mixture obtained in the first step;
   c. in a third step, a compound chosen from the members of the dialdehyde family, previously dissolved in an aqueous buffer of basic pH or in an organic solvent, or in a mixed (organic solvent/water) solvent, is added to the mixture obtained in the second step;
   d. in a fourth step, an induced fluorescence of the mixture obtained in the third step is measured at a wavelength comprised between 390 and 490 nm after excitation at a wavelength comprised between 300 to 350 nm;
   e. in a fifth step, a value of the fluorescence obtained in the fourth step is referred to a calibration curve previously established under the same conditions.

2. Method according to claim 1, wherein in the first step the buffer of the solution for dissolving the sample to be tested is a phosphate buffer at a concentration comprised between 2 mM and 60 mM.

3. Method according to claim 1, wherein in the first step, the solution for dissolving the sample to be tested has a pH comprised between 2 and 6.

4. Method according to claim 1, wherein in the first step the primary activating agent of the carbons bearing the carboxylic functional groups is chosen from the compounds of the carbodiimide family, advantageously from 1-ethyl-3-(3-dimethylaminopropyl)-carbodiimide (EDC) or N-cyclohexyl-N'-(2-morpholinoethyl)carbodiimide methyl-p-toluene sulphonate (CMC), or also N,N'-dicyclohexylcarbodiimide (DCC), N,N'-diisopropylcarbodiimide (DIC), bis(trimethylsilyl)carbodiimide (BTSC), preferably EDC or CMC, very preferably EDC.

5. Method according to claim 1, wherein in said first step, the primary activating agent is at a concentration comprised between 0 and 100 mg per ml of sample to be analyzed.

6. Method according to claim 1, wherein in the first step, the secondary activating agent of the primary activating agent described previously, is chosen from NHS (N-hydroxysuccinimide) or 1-hydroxybenzotriazole (HOBT) or tetrafluorophenol (TTP), 1-hydroxy-7-aza-benzotriazole (HOAT), preferably HOAT.

7. Method according to claim 1, wherein in said first step, the secondary activating agent is at a concentration comprised between 0 and 50 mg per ml of sample to be analyzed.

8. Method according to claim 1, wherein in the first step, the mixture is incubated for a time comprised between 2 and 8 minutes.

9. Method according to claim 1, wherein in the second step the fluorescent primary amine is added at a final concentration comprised between 0 and 100 mg per ml of sample to be analyzed.

10. Method according to any claim 1, wherein the mixture obtained in the second step is at a pH comprised between 5.5 and 11.0.

11. Method according to claim 1, wherein in the second step the fluorescent primary amine is a compound of the benzofurazan family, or the aminophenanthrene family, or the coumarin family, or the "dansyl" derivatives family, N-1-ethylenediaminonaphthalene (EDAN), or 5-aminofluorescein (5-AF), or monodansylcadaverine (MDC) or Nile blue chloride (NBCl), preferably EDAN.

12. Method according to claim 1, wherein in said second step, the dissolution buffer of the fluorescent primary amine is a borate buffer.

13. Method according to claim 1, wherein in said third step, the compound chosen from the members of the dialdehyde family is chosen from naphthalene-2,3-dicarboxyaldehyde (NDA) or o-phthaldialdehyde (OPA), preferably OPA.

14. Method according to claim 1, wherein in said third step, the member of the dialdehyde family is dissolved in an organic solvent, very preferably in ethanol.

15. Method according to claim 1, wherein in said third step, the basic-pH aqueous buffer is chosen from a borate solution, a phosphate solution or a sodium hydrozide solution.

16. Method according to claim 1, wherein in said third step, the mixed solvent is at a pH comprised between 5 and 9.

17. Method according to claim 16, wherein the pH of the mixed solvent is adjusted with an organic or inorganic base.

18. Method according to claim 17, wherein the organic or inorganic base is chosen from a borate solution, a phosphate solution or a sodium hydroxide solution.

19. Method according to claim 1, wherein in said third step, the organic solvent constituting the mixed (organic solvent/water) solvent is advantageously chosen from any water-miscible organic solvent, preferably ethanol.

20. Method according to claim 1, wherein in said third step, the dialdehyde is at a concentration comprised between 0 and 200 mg per ml of sample to be analyzed.

21. Method according to claim 1, wherein in the fifth step, a reference carboxylic acid for establishing the calibration curve is chosen from any monocarboxylic acid, such as for example acetic acid, propionic acid, butyric acid, valeric acid, formic acid, lactic acid, p-hydroxybenzoic acid, preferably acetic acid.

22. Kit for the identification, characterization and quantification by a single detection of the carboxylic functional groups contained in a sample, comprising
    a. at least one primary activating agent of the carbons bearing the carboxylic functional groups;
    b. at least one fluorescent primary amine;
    c. at least one compound of the dialdehyde family;
    d. at least one pH-modulator buffer.

23. Kit for the identification, characterization and quantification by a single detection of the carboxylic, thiol and amine functional groups contained in a sample, comprising
    a. at least one primary activating agent of the carbons bearing the carboxylic functional groups;
    b. at least one fluorescent primary amine;
    c. at least one compound of the dialdehyde family;
    d. at least one non-fluorescent amine;
    e. at least one pH-modulator buffer;
    f. at least one non-fluorescent thiol.

24. Method according to claim 1, wherein in the first step, the solution for dissolving the sample to be tested has a pH comprised between 3.0 and 4.0.

25. Method according to claim 1, wherein in the second step the fluorescent primary amine is added at a final concentration comprised between 25 and 50 mg per ml of sample to be analyzed.

* * * * *